United States Patent
Moran

(10) Patent No.: US 6,402,958 B1
(45) Date of Patent: Jun. 11, 2002

(54) CHROMATOGRAPHY COLUMN LOADING METHOD

(75) Inventor: Michael G. Moran, Danville, NH (US)

(73) Assignee: UOP LLC, Des Plaines, IL (US)

( * ) Notice: Subject to any disclaimer, the term of this patent is extended or adjusted under 35 U.S.C. 154(b) by 56 days.

(21) Appl. No.: 09/641,047

(22) Filed: Aug. 17, 2000

(51) Int. Cl.⁷ .............................................. B01D 15/08
(52) U.S. Cl. ...................... 210/656; 210/198.2; 141/12; 141/80
(58) Field of Search ................................. 210/635, 656, 210/659, 198.2; 141/12, 80

(56) References Cited

U.S. PATENT DOCUMENTS

| | | | | |
|---|---|---|---|---|
| 3,703,798 A | * | 11/1972 | Pretorius | 210/198.2 |
| 4,175,037 A | * | 11/1979 | Benney | 210/198.2 |
| 4,208,284 A | * | 6/1980 | Pretorius | 210/198.2 |
| 4,636,315 A | * | 1/1987 | Allen | 210/198.2 |
| 4,670,141 A | * | 6/1987 | Shackelford | 210/198.2 |
| 4,719,011 A | * | 1/1988 | Shalon | 210/198.2 |
| 4,797,209 A | * | 1/1989 | Jackson | 210/198.2 |
| 4,861,473 A | * | 8/1989 | Shackelford | 210/198.2 |
| 4,882,047 A | * | 11/1989 | Shalon | 210/198.2 |
| 4,888,112 A | * | 12/1989 | Kronwald | 210/198.2 |
| 5,013,433 A | * | 5/1991 | Shalon | 210/198.2 |
| 5,021,162 A | * | 6/1991 | Sakamoto | 210/198.2 |
| 5,169,522 A | | 12/1992 | Shalon et al. | 210/198.2 |
| 5,363,886 A | * | 11/1994 | Ashraf-Khorassani | 210/656 |
| 5,866,008 A | | 2/1999 | Shalon et al. | 210/656 |

OTHER PUBLICATIONS

Shalon, Y. A Spring–Loaded Preparative HPLC Column *American Laboratory* (Sep. 1997) 4 pages.

* cited by examiner

*Primary Examiner*—Ernest G. Therkorn
(74) *Attorney, Agent, or Firm*—John G. Tolomei; Frank S. Molinaro; Maryann Maas

(57) ABSTRACT

An adsorbent bed is loaded into an HPLC column by a method which comprises fluidization of the adsorbent. The adsorbent may be added as a slurry which is then fluidized and not allowed to settle. The adsorbent bed is then immediately compressed.

7 Claims, No Drawings

CHROMATOGRAPHY COLUMN LOADING METHOD

FIELD OF THE INVENTION

The invention relates to a method of loading adsorbent into chromatographic columns used in small to medium scale separations of chemicals such as chiral chemicals and pharmaceuticals.

BACKGROUND OF THE INVENTION

Chromatographic separation is a highly useful method of separating a mixture of two or more compounds which are not readily separated by other means such as fractional distillation. During a chromatographic separation this mixture is injected into a bed of an adsorbent or stationary phase. This material is chosen for its ability to selectively retain one of the compounds more strongly than the other. A continuous stream of a fluid referred to as the solvent or mobile phase is slowly passed through the bed, and the less strongly retained compounds(s) gradually moves through the bed faster than the other compound(s). This gradually forms two or more "peaks", each having a higher concentration of the respective compound(s) and which are withdrawn separately.

These separations are promoted by long beds of adsorbent which are free from voids and packing irregularities which would tend to cause backmixing of the fluids flowing through the bed. The method used to pack the adsorbent into the long tubes used to perform the separation is important, and the importance increases as the diameter of the tube is increased to accommodate higher fluid rates needed for higher capacity separations.

RELATED ART

U.S. Pat. No. 5,013,433 issued to Y. Shalon describes a chromatographic column characterized as having a zero void volume. The invention centers upon the construction of the distribution and collection devices located at the ends of the column for assuring uniform flow of the liquid through the column.

U.S. Pat. No. 5,169,522 issued to Y. Shalon et al. describes a hydraulically active liquid chromatography column suitable for use in HPLC systems. A cylindrical bed of adsorbent is retained within an adsorbent chamber and is compressed by a piston driven by a hydraulic fluid in the hydraulic chamber. An opening is provided in the end plate of the apparatus for enabling the monitoring, maintaining and releasing of the pressure in the column as necessary. This opening may be equipped with a gauge and valve.

An article by Yehuda Shalon printed in the magazine *American Laboratory* in September 1997 describes problems encountered in loading chromatographic columns including packed columns. FIG. 2 of the article illustrates a spring-loaded HPLC column said to reduce these problems. The piston applying pressure to the cylindrical bed of adsorbent may be driven downward through a threaded screw at an upper end of the column. A compressed spring intermediate the piston and the threaded screw acts directly on the piston. The spring maintains a relatively constant pressure upon the bed of adsorbent.

U.S. Pat. No. 5,866,008 issued to Y. Shalon et al. describes an apparatus and method for loading high-pressure chromatographic columns. In column 10, it is stated the slurry medium can be agitated before compression by rocking the column about rotating joint 42.

BRIEF SUMMARY OF THE INVENTION

The invention is a method to densely load adsorbent into small adsorptive separation columns used in performing high-pressure liquid chromatographic separations. The invention includes a step in which the adsorbent is fluidized to remove irregularities and voids from the adsorbent bed while the adsorbent is being loaded into the column or after it is in the column.

One broad embodiment of the invention may be characterized as a method for loading a particulate adsorbent into a column used for chromatographic separation comprising placing a quantity of adsorbent into a cylindrical column; fluidizing the adsorbent by the upward passage of a liquid through the column, and compressing the adsorbent by use of a piston located within the column.

DETAILED DESCRIPTION AND PREFERRED EMBODIMENTS

High-pressure liquid chromatography is an established tool for the small-scale separation of many chemicals. It is used in research facilities and in commercial production plants. In order to employ this separation technique it is necessary to have a column containing a uniformly loaded bed of a suitable adsorbent. While at first glance it may appear rather easy to provide such a packed bed in a small diameter cylinder, there are serious and costly problems as described in the previously cited article from *American Laboratory*. The bed of adsorbent must be packed in a uniform manner with no variations in particle size distribution or stratification's of particles. These problems are compounded by the very small size of the adsorbent particles, which are often less than 50 microns in diameter. The result has been the development of certain loading techniques referred to in the article as slurry packing and various methods to compress the bed by a hydraulic ram or press. Slurry packing has been demonstrated to provide significantly higher column efficiencies than dry packing. A bed loaded by either method is still compressed to minimize random void volumes.

The traditional small diameter metal tubes used as adsorbent chambers in high-pressure liquid chromatography (HPLC) have internal diameters up to about two cm. The traditional silica supported HPLC adsorbents can be loaded and then packed to a very high pressure in these small diameter cylinders. For example, the applied pressure may reach 30,000 psi during the packing operation. This results in a very compacted almost solid bed of adsorbent which may be simply sealed off and used. However, as the desired capacity of the process unit increases it is necessary to increase the cross sectional area of the adsorbent chambers to accommodate more adsorbent. At a certain point, it becomes impractical to load and compress the adsorbent in the same manner as in these small diameter chambers. The art has therefore developed alternative means to insure the integrity of the adsorbent bed. These have included the methods described above.

When high pressure liquid chromatography is applied to larger quantity separations or when a larger column is required due to the need to process a dilute solution the problems of properly loading the adsorbent into the column worsen. For instance, problems develop in employing the slurry packing method to larger columns such as those greater than about 8 cm in diameter. The adsorbent particles often settle out of the carrier fluid or "solvent" very quickly. When the adsorbent has a broad particle size distribution, greater than a 2 micron deviation from the mean diameter, there can be undesirable stratification due to faster settling of larger particles. It is an objective of the subject invention to provide an improved method for loading larger diameter high-pressure liquid chromatographic columns.

In the subject method, this objective is achieved by a fluidization of the adsorbent particles prior to a final compression of the bed to near its theoretical limit. This fluidization of the particles is subject to considerable variation but certain parameters can be set. The fluidization must be performed at a rate and time which prevents any portion of the bed from settling in an undesirable manner. Further, the fluidization must be of the entire bed. That is the upward liquid velocity must be sufficient to lift all of the particles regardless of the density or diameter.

The frits and other fluid transfer and distribution systems associated with the column for use as a chromatographic column are preferably used to the maximum extent possible during the fluidization. This minimizes the need for added equipment. A preferred fluidization media is the liquid used in the slurry which transports the adsorbent into the column. This media, or solvent, used to fluidize the adsorbent may be charged to the bottom of the column through the normal column outlet and distributed by the liquid collection frit normally present at the bottom of the column. This will help distribute the solvent and eliminate dead spots by ensuring that all of the adsorbent is subjected to the upward liquid flow. The solvent can be removed through the outlet line at the top of the column usually used as the feed inlet. Columns may have several other openings at their ends for the passage of fluid streams during either loading or operation and which can be employed during the adsorbent fluidization.

Allowing the slurry to settle in the column may make it more difficult to fluidize. A constant upward flow of solvent through the column during the placement of the adsorbent in the column is therefore preferred. The fluidizing solvent exiting the column can be collected and recycled to the bottom of the column. The upward solvent flow should be continued at least until the piston used to compress the adsorbent bed begins to move downward against the upper portion of the bed. The upward solvent flow can be reduced or stopped at this time. However, if feasible the upward flow through the adsorbent bed is continued during the initial phases of compression during which the volume of the bed is reduced.

Columns loaded by the subject process may be used singularly or they may be used in separation systems requiring multiple columns such as simulated moving bed (SMB) systems. Simulated moving bed adsorptive separation is used commercially in a number of industries to perform useful separations of a variety of chemicals including petrochemical intermediates. It is established as a leading industrial process for the large-scale recovery of paraxylene suitable for the manufacture of polyesters. It is also a leading process for the recovery of normal paraffins used in the production of linear olefins which are then consumed as detergent precursors. SMB adsorptive separation is also being employed as a tool in the separation of a wide variety of other chemicals including chiral compounds and intermediates used in the production of experimental and therapeutic drugs. These latter separations are normally conducted in small to intermediate scale pilot plants not requiring much feed stock, adsorbent or plant space. This is especially true when the materials which are to be separated are expensive due to their rarity or complicated production techniques.

In the simulated moving bed technique the normal chromatographic profiles which develop as a multi-component feed mixture passes through a lengthy bed of adsorbent are in effect frozen within the apparatus by the periodic advancement in the location of the respective addition and withdrawal points of the feed, desorbent (mobile phase), extract and raffinate streams. During an SMB process the location at which the feed stream and the desorbent stream enters the overall process is slowing changed in a stepwise manner. All of the adsorbent chambers are linked together serially in a continuous flow path and the feed and desorbent streams push the liquid contents of several chambers through the apparatus. A shift of the feed and withdrawal points in the direction of fluid flow simulates movement of solids in the opposite direction. Careful control of flow rates and transfer point changes allows an effective stationary phase-mobile phase pair to provide a continuous high-purity product stream.

The use of SMB techniques is described in U.S. Pat. Nos. 2,985,589; 3,310,486; 3,392,113 and 4,475,954 which are incorporated herein by reference for their description of the operation of the SMB process and equipment for its performance. The process uses a plurality of serially connected adsorbent chambers, with the number of chambers in any one zone of the process depending on such factors as adsorbent performance, desorbent strength, etc. The adsorbent chambers used are serially interconnected by a circuit of conduits and valves. This interconnection forms a loop containing all of the beds, with a point or points to add and remove the primary process streams between each bed located at regular intervals along the loop. U.S. Pat. No. 3,706,812 issued to A. J. De Rosset and R. W. Neuzil describes a pilot plant scale simulated moving bed adsorptive separation process unit. U.S. Pat. No. 5,565,104 to J. W. Priegnitz and U.S. Pat. No. 5,635,072 to M. G. Moran illustrate other valve arrangements for small scale simulated moving bed adsorptive separation units and are incorporated herein for that teaching.

The separation of racemic mixtures of chiral material by continuous simulated moving bed adsorptive separation was described in a presentation conducted at PREP '91 in Arlington, Va., USA on May 13–15, 1991 and printed in the *Journal of Chromatography*, 590 (1992) pages 113–117. The article gives a diagram of a small scale system with eight adsorbent columns and four rotary valves.

Difficulties also arise in performing an HPLC separation using SMB techniques due to the very small particle size (approx. 10–20 microns) of the currently available chiral stationary phases. This small size results in a very high-pressure drop through the adsorbent bed. The small size particles are also more subject to channeling of the fluid flows which allows some fluid to move faster and bypass adsorbent. This disrupts the desired composition profiles in the flowing process fluid and lowers the performance, e.g., product purity, of the system. Compressing and packing of the adsorbent bed is intended in part to minimize this tendency toward channeling.

The adsorbent particles located in the adsorbent chamber may be in any shape, e.g., sphere, granule, irregular particle or extrudate, and of any size suitable for use in high-pressure liquid chromatography. It is highly preferred the particles are spherical. The composition of the adsorbent is not a controlling factor in the invention, which may employ any suitable solid adsorbent. Examples of possible adsorbent material include the cross-linked organic resins, natural or synthetic zeolites including zeolites X, Y, L, ZSM, Beta and omega, silica, silica-alumina, the various adsorptive aluminas, pillared and mesoporous materials including pillared clays, and nonzeolitic molecular sieves (NZMS), such as silica aluminophosphates and aluminophosphates, and proprietary chiral stationary phases. Suitable adsorbents for specific separations are available commercially from a number of suppliers. Chiral stationary phases are described in U.S. Pat. Nos. 5,254,258; 5,290,440 and 5,88,180. Further information specific to the separation of chiral compounds may be obtained from U.S. Pat. No. 5,518,625 which is incorporated herein by reference. The adsorbent particles used in the column preferably have an average particle diameter less than 50 microns.

The apparatus used in performing an SMB process, including the subject adsorbent loading method, can be constructed from commercially available components. Suitable valves and actuators for an SMB process are available commercially. The conduits and connectors may be of standard design used for pilot to intermediate scale pharmaceutical plants or HPLC instruments used for the desired separation in the relevant industry. The adsorbent chambers may be made from carbon or stainless steel or other metals as dictated by mechanical and process design factors.

A preferred embodiment of the subject invention can accordingly be characterized as a method for loading a particulate adsorbent into a column used for chromatographic separation, which method comprises passing a slurry of adsorbent particles into a cylindrical column, with the carrier fluid of the slurry exiting the column and leaving the a cylindrical bed of adsorbent particles within the column; fluidizing the bed of adsorbent particles within the column by the upward passage of a liquid through the column, and then compressing the bed of adsorbent particles.

Operating conditions for columns loaded according to the subject process include a temperature of about −50 to 300 degrees C., preferably 20 to about 100 degrees C. It is generally preferred that the column is operated with a positive inlet pressure in the general range of about 700 to 25000 kPa. If the column is employed in an SMB-type separation then the pressure at the inlet to the chamber will vary as the process "steps" through the simulated moving bed cycle. Depending on operating mode, the pressure will be highest when the mobile phase or feed is being charged directly into the column as the entry point in the process. The pressure at the inlet may therefore vary during the performance of the separation. A range of from 3000 psig to about 100 psig is possible.

Representative feed stream flow rates for a small-scale SMB unit are 0.1–2.0 ml/min for the feed and 2–20 ml/min for the desorbent. Such units would employ conduits having internal diameters of about 0.3 to about 0.6 cm and could produce several hundred kg/year or more of dry product depending on the ease of separation. Intermediate scale pharmaceutical units would have quite a bit larger flow rates, with the maximum feed flow rate being limited only by equipment and economic considerations. The total amount of dry product recovered from the extract in these units could reach 1000 kg/day. The subject invention finds its greatest utility in adsorbent columns having diameters greater than about 10 cm. The columns in intermediate scale units may have diameters up to 100 cm or more.

As previously mentioned chromatographic separations can be applied to a wide range of chemical compounds. Rather unusual chemicals such as chiral pharmaceutical intermediates are just one example. Fermentation broths are another. Non-chiral alkyl aromatics, halogenated aromatic compounds or aromatic compounds containing heteroatoms may also be separated using the subject invention. The aromatic compounds may have from one to four or more benzene rings and two or more alkyl groups per ring structure. Compounds having a ring structure other than a benzene ring can be separated in this apparatus. Naphthalenes and indanes are suitable feeds as are oxygenated aromatics such as ethers, esters, alcohols and carbohydrates including saccharides. Organic acids, proteins and amino acids are other classes of suitable feed compounds. The subject process can be used in the separation of one specific compound from a mixture or for the separation of a class of compounds from one or more classes of different compounds.

What is claimed is:

1. A method for loading a bed of particulate adsorbent into a column used for chromatographic separation, which method comprises:
   a) placing a quantity of adsorbent into a cylindrical column;
   b) fluidizing the adsorbent by the upward passage of a liquid through the column, and;
   c) compressing the adsorbent by use of a piston located within the column.

2. The method of claim 1 wherein the fluidization of the adsorbent is continued during the initial portion of the compression of the adsorbent.

3. A method for loading a particulate adsorbent into a column used for chromatographic separation comprising:
   a) passing a slurry of adsorbent particles into a cylindrical column, with the carrier fluid of the slurry exiting the column and leaving a cylindrical bed of adsorbent particles within the column;
   b) fluidizing the bed of adsorbent particles within the column by the upward passage of a liquid through the column, and then;
   c) compressing the bed of adsorbent particles.

4. The method of claim 3 wherein the slurry is passed downward into the column in the same direction as a process feed stream is subsequently passed through the column.

5. The method of claim 4 wherein the liquid used to fluidize the adsorbent particles is recycled through the column.

6. The method of claim 3 wherein the adsorbent particles have an average particle diameter less than 50 microns.

7. The method of claim 3 wherein the fluidization of the adsorbent is continued during the initial portion of the compression of the adsorbent.

* * * * *